United States Patent
O'Brien et al.

(10) Patent No.: US 8,408,212 B2
(45) Date of Patent: Apr. 2, 2013

(54) CERVICAL OCCLUDER

(75) Inventors: John M. O'Brien, Lexington, KY (US); Dirk V. Hoyns, Jackson, GA (US)

(73) Assignee: Glenveigh Medical, LLC, Chatanooga, TN (US)

( * ) Notice: Subject to any disclaimer, the term of this patent is extended or adjusted under 35 U.S.C. 154(b) by 558 days.

(21) Appl. No.: 12/543,397

(22) Filed: Aug. 18, 2009

(65) Prior Publication Data

US 2010/0043802 A1 Feb. 25, 2010

Related U.S. Application Data

(60) Provisional application No. 61/089,609, filed on Aug. 18, 2008.

(51) Int. Cl.
*A61F 6/06* (2006.01)
*A61F 2/24* (2006.01)
*A61M 29/00* (2006.01)
*A61B 5/103* (2006.01)

(52) U.S. Cl. ........ 128/830; 606/193; 600/591; 623/2.14

(58) Field of Classification Search .................. 128/898, 128/830, 831, 833, 834, 845; 606/200, 213, 606/151, 144, 1, 108, 139, 148, 153, 232, 606/191–198; 623/1.24, 2.14, 2.15, 2.16, 623/2.17, 2.18, 2.19, 1.25, 1.26, 2.1, 2.12
See application file for complete search history.

(56) References Cited

U.S. PATENT DOCUMENTS

| | | | |
|---|---|---|---|
| 4,655,771 A | 4/1987 | Wallstén | |
| 4,954,126 A | 9/1990 | Wallstén | |
| 5,026,377 A | 6/1991 | Burton et al. | |
| 5,061,275 A | 10/1991 | Wallstén | |
| 5,484,444 A | 1/1996 | Braunschweiler | |
| 5,613,950 A | 3/1997 | Yoon | |
| 6,350,463 B1 | 2/2002 | Herman et al. | |
| 6,375,970 B1 | 4/2002 | Bieniarz | |
| 6,464,712 B1 | 10/2002 | Epstein et al. | |

(Continued)

FOREIGN PATENT DOCUMENTS

| | | |
|---|---|---|
| CN | 102368966 | 3/2012 |
| EP | 1046375 A1 | 10/2000 |

(Continued)

OTHER PUBLICATIONS

International Application Serial No. PCT/US2009/004707, International Search Report mailed Nov. 23, 2009 6 pgs.

(Continued)

*Primary Examiner* — Patricia Bianco
*Assistant Examiner* — Tarla Patel
(74) *Attorney, Agent, or Firm* — Schwegman Lundberg Woessner P.A.

(57) ABSTRACT

Apparatus, methods and kits which, when installed or used, occlude or partially occlude a cervical canal, the internal opening of a cervical canal (cervical os), or a uterine side wall rupture location, such as to inhibit or prevent bacterial access and retard leakage of amniotic fluid resulting from PROM. The present apparatus can include an expandable support member of a biocompatible and non-toxic material. In some examples, the support member can include a top portion having a first diameter and a bottom portion having a second diameter less than the first diameter. In some examples, the support member can include an expandable stent of a suitable length and uniform diameter to be inserted in a non-dilated cervical canal or transabdominal access route. In various examples, the apparatus further includes a fluid-resistant fabric, polymer, substance or other material placed over at least the top portion of the support member.

19 Claims, 14 Drawing Sheets

U.S. PATENT DOCUMENTS

| | | |
|---|---|---|
| 2003/0219492 A1 | 11/2003 | Berry |
| 2004/0220610 A1* | 11/2004 | Kreidler et al. ............... 606/200 |
| 2005/0192616 A1* | 9/2005 | Callister et al. ............... 606/193 |
| 2007/0066993 A1 | 3/2007 | Kreidler |

FOREIGN PATENT DOCUMENTS

| | | |
|---|---|---|
| WO | WO-00/27292 | 5/2000 |
| WO | WO-0027292 | 5/2000 |
| WO | WO-2008/046050 A2 | 4/2008 |
| WO | WO-2008046050 A2 | 4/2008 |
| WO | WO-2010/021695 A1 | 2/2010 |
| WO | WO-2010021695 A1 | 2/2010 |

OTHER PUBLICATIONS

International Application Serial No. PCT/US2009/004707, Written Opinion mailed Nov. 23, 2009, 8 pgs.

"Gore Helex Septal Occluder", [online]. © 2002-2007 W. L. Gore & Associates, Inc. [archived Aug. 19, 2007]. Retrieved from the Internet: <URL: http://web.archive.org/web/20070819114625/http://www.gorernedical.com/helex/index#>, (2007), 1 pg.

Drakeley, A. J., et al., "Cervical stitch (cerclage) for preventing pregnancy loss in women (Review)", *Cochrane Database Syst. Rev.*, (1), (The Cochrane Collaboratione®), (2003), 38 pgs.

Vidaeff, A. C., et al., "Fetal pulse oximetry: 8 vital questions", *OBG Management*, 16(3), (Mar. 2004), 28-44.

"European Application Serial No. 09789160.0, Response filed Sep. 19, 2011 to Office Action mailed May 11, 2011", 12 pgs.

"International Application Serial No. PCT/US2009/004707, International Search Report mailed Nov. 23, 2009", 6 pgs.

"International Application Serial No. PCT/US2009/004707, Written Opinion mailed Nov. 23, 2009", 6 pgs.

\* cited by examiner

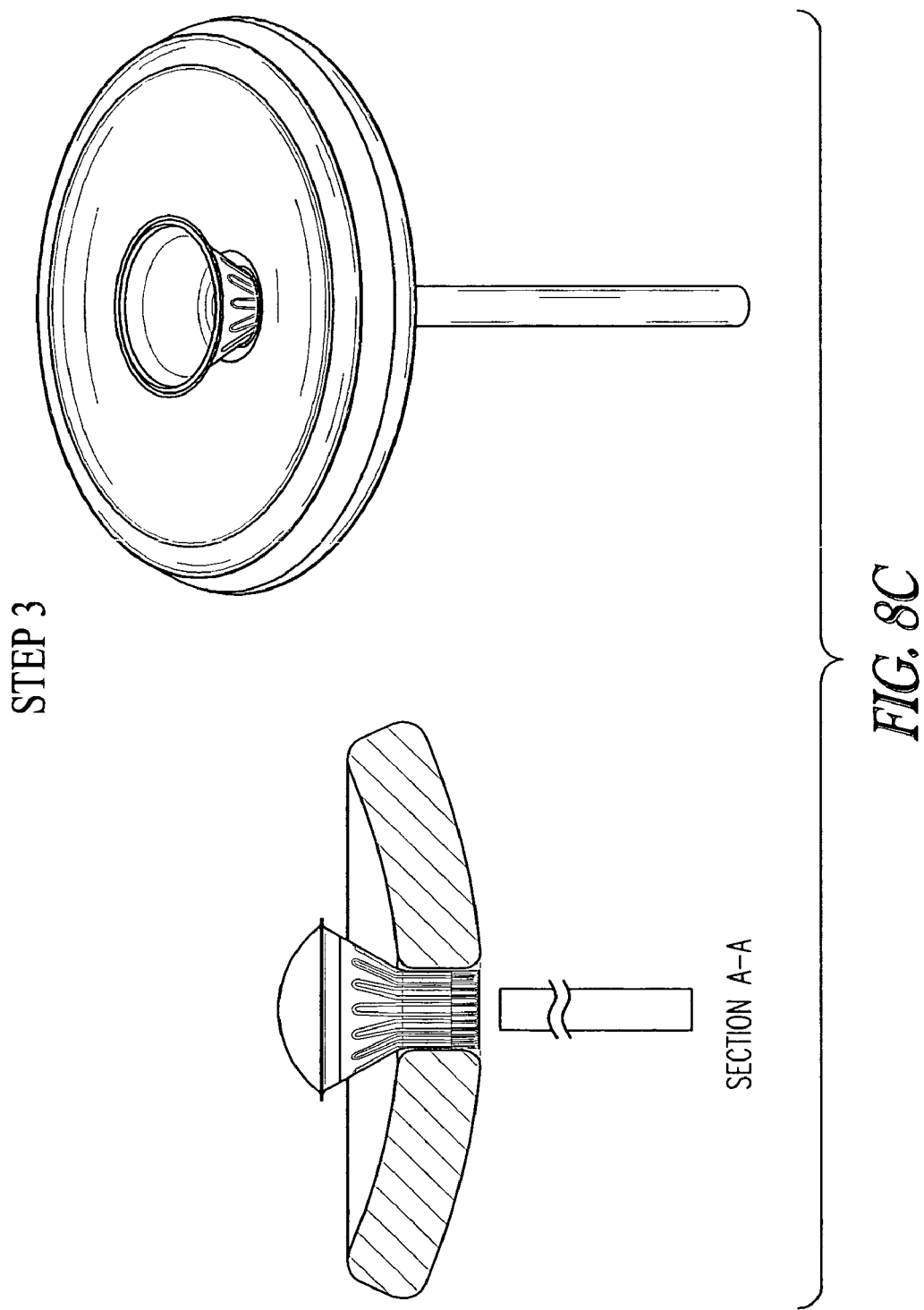

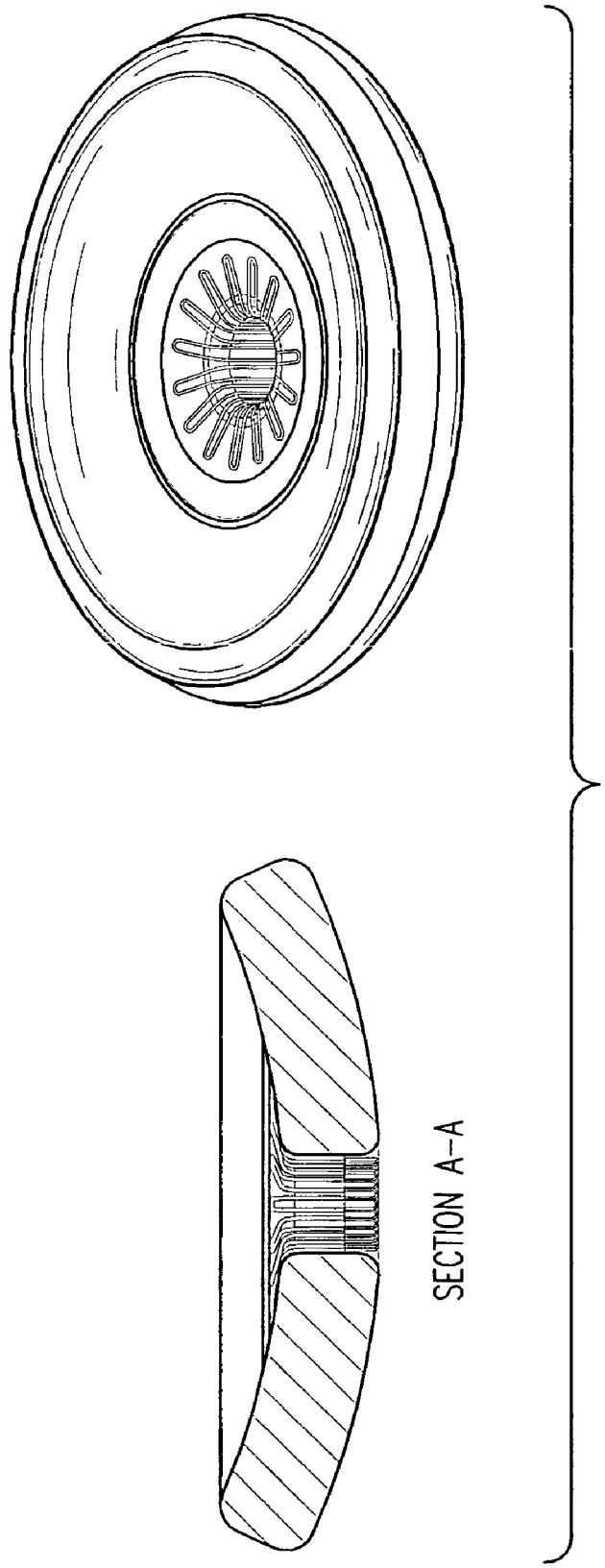

CERVICAL OCCLUDER

CLAIM OF PRIORITY

This non-provisional patent application claims the benefit of priority under 35 U.S.C. §119(e) to U.S. Provisional Patent Application Ser. No. 61/089,609, entitled CERVICAL OCCLUDER, filed on Aug. 18, 2008, which is hereby incorporated by reference in its entirety.

TECHNICAL FIELD

This patent document pertains generally to apparatus and methods to treat physiological conditions of pregnancy. More particularly, but not by way of limitation, this patent document pertains to apparatus, methods and kits which, when installed or used, occlude or partially occlude a cervix or other location of membrane rupture to contain amniotic fluid within the uterine cavity.

BACKGROUND

Premature rupture of membranes (PROM), as it relates to pregnancy, is the rupture of an amniotic membrane enclosing a fetus before the onset of labor. In most cases, PROM occurs near term, but when membrane rupture occurs before 37 weeks gestation, it is referred to as preterm-PROM (PPROM) or simply PROM. PROM complicates approximately 3-4% of pregnancies and leads to 30-40% of all preterm births— approximately 150,000 cases annually in the United States (US) alone.

PROM is most commonly caused by a bacterial infection, by smoking, or by a defect in the structure of the amniotic membrane, uterus, or cervix. This condition is termed spontaneous PROM. In rare cases, the rupture can heal, but in most cases of preterm PROM, labor begins within one week after rupture. Accordingly, one of the most common complications of preterm PROM is premature delivery and its associated risks, including perinatal and neonatal complications. Neonates surviving preterm PROM may develop sequelae, such as malpresentation, cord compression, oligohydramnios, necrotizing enterocolitis, neurologic impairment, intraventricular hemorrhage, or respiratory distress syndrome, and 1-2% even face the risk of fetal death. These sequelae are most common when PROM occurs before 32 weeks gestation and results in premature delivery.

PROM can also be the result of iatrogenic causes due to surgical manipulations during pregnancy. Fetoscopic procedures, amniocentesis, and amnioreduction are associated with a risk for PROM.

Overview

The present inventors have recognized, among other things, that it would be useful to provide a means to not only prolong pregnancy and advance fetal development, particularly when PROM occurs before 32 weeks, but to also prevent continuing leakage of amniotic fluid while pregnancy is prolonged, such as to reduce or minimize adverse fetal outcomes.

The present apparatus is configured to occlude or partially occlude a cervical canal, the internal opening of the cervical canal (cervical os), or a uterine side wall rupture location, such as to inhibit or prevent bacterial access and leakage of amniotic fluid resulting from PROM. The present apparatus can include an expandable scaffold, frame, cage or stent, or other support member of a biocompatible and non-toxic material. In some examples, the support member can include a top portion having a first diameter and a bottom portion having a second diameter less, which is less than the first diameter. In some examples, the support member can include an expandable stent of a suitable length and substantially uniform diameter to be inserted into a non-dilated cervical canal. The support member can be self-expanding or actively expandable, such as by a catheter-delivered balloon.

In various examples, the apparatus further includes a fluid-resistant fabric, polymer, mesh, substance or other material placed over or otherwise coupled to at least the top portion of the support member (i.e., an innermost portion of the support member, which, when implanted, is inserted nearest to the internal cervical os). Fluid-resistant materials can include water-resistant, water-impermeable, fluid-impermeable or similarly impervious or repellant materials. The fluid-resistant material can be made of any biocompatible and non-toxic material, such as GORE-TEX® or other tightly woven fluid-resistant, nano-fiber material, polytetrafluoroethylene (PTFE), or expanded PTFE. In some examples, the fluid-resistant material includes a coating, such as a silicone-coated material.

In operation, a method of using the present apparatus or kits can include temporarily occluding or partially occluding a cervical canal, an internal cervical os, or a uterine side wall rupture location to extend pregnancy after PROM. The method can comprise inserting into the cervical canal for spontaneous PROM or through an abdominal wall for iatrogenic PROM, an expandable support member that has been covered, coated or otherwise coupled on at least a top side portion with a fluid-resistant material. The methodology may also be employed in an effort to prevent fluid loss after fetoscopic manipulations within the uterus to minimize the frequency of post-operative PROM.

To better illustrate the apparatus, methods and kits disclosed herein, a non-limiting list of examples is provided here:

In Example 1, an implantable occlusion apparatus comprises an expandable support member extending from a first end portion to a second end portion, the expandable support member sized to pass through a cervical canal or a transabdominal access route and be positioned within at least one of an amniotic membrane, a cervical os, or a uterine side wall; and at least one fluid-resistant material coupled to at least a first end portion of the expandable support member, wherein the fluid-resistant material is configured to occlude or partially occlude the cervical os or a rupture of the amniotic membrane near the uterine side wall.

In Example 2, the apparatus of Example 1 is optionally configured such that the expandable support member includes a stent-like structure having a uniform diameter from the first end portion to the second end portion.

In Example 3, the apparatus of any one or any combination of Examples 1 or 2 is optionally configured such that the fluid-resistant material is coupled to the first end portion of the expandable support member via one or more crimps or stitches.

In Example 4, the apparatus of any one or any combination of Examples 1-3 is optionally configured such that the at least one fluid-resistant material includes a first and a second fluid-resistant material, the first fluid-resistant material covering or coated on the first end portion of the expandable support member, and the second fluid-resistant material spaced from, and coupled to, the first end portion of the expandable support member.

In Example 5, the apparatus of Example 4 is optionally configured such that a bottom surface of the second fluid-resistant material is coated with a water-activated adhesive.

In Example 6, the apparatus of any one or any combination of Examples 1-5 is optionally configured such that the first end portion of the expandable support member includes a greater diameter than the second end portion of the expandable support member.

In Example 7, the apparatus of Example 6 is optionally configured such that the first end portion is configured to support the fluid-resistant material and the second end portion is configured to anchor against a wall of the cervical canal or the transabdominal access route.

In Example 8, the apparatus of any one or any combination of Examples 1-7 is optionally configured such that the fluid-resistant material extends at least partially down a length of the expandable support member.

In Example 9, the apparatus of any one or any combination of Examples 1-8 is optionally configured such that the second end portion of the expandable support member includes an expanded diameter between about 0.25 cm to about 2.0 cm and a pre-expanded diameter between about 3 mm to about 8 mm.

In Example 10, the apparatus of any one or any combination of Examples 1-9 is optionally configured such that the fluid-resistant material includes an average, implanted diameter between about 3 cm to about 4 cm.

In Example 11, the apparatus of any one or any combination of Examples 1-10 is optionally configured such that the fluid-resistant material includes an average implanted diameter between about 0.75 cm to about 1.25 cm.

In Example 12, the apparatus of any one or any combination of Examples 1-11 is optionally configured such that the expandable support structure includes a shape-memory alloy.

In Example 13, the apparatus of any one or any combination of Examples 1-12 is optionally configured such that the fluid-resistant material includes polytetrafluoroethylene or expanded polytetrafluoroethylene.

In Example 14, the apparatus of any one or any combination of Examples 1-13 is optionally configured such that the fluid-resistant material includes a tightly woven fluid-resistant, nano-fiber material.

In Example 15, the apparatus of any one or any combination of Examples 1-14 is optionally configured such that a seal between the fluid-resistant material and adjacent bodily tissue includes sufficient adherence to withstand a pressure of about 20 mmHg or more without substantial fluid leakage through the cervical os.

In Example 16, the apparatus of any one or any combination of Examples 1-15 is optionally configured such that the fluid-resistant material is resistant to fluid penetration in a first direction and permits fluid penetration in a second direction, opposite the first direction.

In Example 17, the apparatus of any one or any combination of Examples 1-16 is optionally configured such that the expandable support member and the fluid-resistant material are configured to conform to changes in tissue structure over time, when implanted.

In Example 18, the apparatus of any one or any combination of Examples 1-17 is optionally configured such that one or both of the expandable support member or the fluid-resistant material is coated or impregnated with an antimicrobial agent.

In Example 19, the apparatus of any one or any combination of Examples 1-18 is optionally configured such that the fluid-resistant material includes at least one pharmaceutical substance.

In Example 20, the apparatus of any one or any combination of Examples 1-18 optionally comprises a reservoir contained at least partially within the expandable support member, the reservoir configured to carry a pharmaceutical substance.

In Example 21, the apparatus of Example 20 comprises the pharmaceutical substance.

In Example 22, the apparatus of any one or any combination of Examples 20 and 21 is optionally configured such that the fluid-resistant material includes at least one pore in fluid communication with the reservoir, the at least one pore having a size and shape configured to control a rate of release of the pharmaceutical substance.

In Example 23, the apparatus of any one or any combination of Examples 20-22 optionally comprises a wick extension secured within the reservoir and in fluid communication with the pharmaceutical substance stored therein.

In Example 24, a method comprises implanting an apparatus including an expandable support member and a fluid-resistant material adjacent at least one of an amniotic membrane, a cervical os, or a uterine side wall, the fluid-resistant material coupled to at least a first end portion of the expandable support member; securing the expandable support member in a cervical canal or an abdominal access route, including expanding one or more portions of the expandable support member to bias against a wall of the cervical canal or the abdominal access route; and providing a replacement membrane at or near an amniotic membrane rupture location, including forming a seal with the fluid-resistant material and the amniotic membrane or a uterine side of the cervical os, to retain amniotic fluid.

In Example 25, the method of Example 24 optionally comprises performing cerclage stitching about the cervix after inserting the apparatus.

In Example 26, the method of any one or any combination of Examples 24 or 25 optionally comprises releasing a pharmaceutical substance stored in a reservoir at least partially positioned within the expandable support member.

In Example 27, the method of Example 26 optionally comprises refilling the reservoir with a pharmaceutical substance.

In Example 28, the method of any one or any combination of Examples 24-27 is optionally configured such that implanting the apparatus includes implanting an apparatus pre-filled with a pharmaceutical substance.

In Example 29, the method of any one or any combination of Examples 24-28 is optionally configured such that implanting the apparatus is approached by a route selected from a transvaginal access route or a transabdominal access route.

In Example 30, the method of any one or any combination of Examples 24-29 optionally comprises removing the apparatus from adjacent the amniotic membrane, the cervical os, or the uterine side wall, including using a retrieval loop at a second end portion, opposite the first end portion, of the expandable support member.

In Example 31, a kit comprises the apparatus according to any one or any combination of Examples 1-23; and a set of instructions for using the apparatus to occlude or partially occlude at least one of an amniotic membrane, a cervical os, or a uterine side wall.

In Example 32, the kit of Example 31 optionally comprises an applicator device having an adjustable mechanical stop to ensure proper implant depth, the applicator device configured to access at least one of the amniotic membrane, the cervical os, or the uterine side wall.

In Example 33, the apparatus, method or kit of any one or any combination of Examples 1-32 is optionally configured such that all elements or options recited are available to use or select from.

These and other examples, advantages, and features of the present apparatus, methods and kits will be set forth in part in following Detailed Description. This Overview is intended to provide non-limiting examples of the present subject matter—it is not intended to provide an exclusive or exhaustive explanation. The Detailed Description is included to provide further information about the present apparatus, methods and kits.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present document.

FIGS. 8A-8E illustrate an example of an apparatus and method of use such as for cervical occlusion.

DETAILED DESCRIPTION

Preterm or premature birth is a complication in approximately 12% of US pregnancies, and about 30-40% of these cases are due to PROM. The causes vary, including inflection, and a number of anatomical or medical conditions are implicated. Twenty-three weeks is considered by many to be the earliest possible gestational age for viability—if PROM occurs before 23 weeks, it will often lead to loss of a fetus through natural or surgical means. Every day of extension of pregnancy can decrease the severity of fetal impairment due to prematurity between 23 and 28 weeks gestation; thus, maximizing the duration of pregnancy is clinically important.

In this patent document, apparatus, methods and kits configured to occlude or partially occlude a cervical canal, an internal cervical os, or a uterine side wall rupture location, such as to inhibit or prevent leakage of amniotic fluid resulting from PROM, are disclosed. The apparatus provides a replacement membrane and potentially a barrier to ascending infection, insertable by a treating physician, which may allow an otherwise abnormal pregnancy to progress normally. It is believed, and initial studies have shown, the apparatus can reduce fetal mortality and morbidity, allow for simple and safe insertion and removal, restore anatomical function, minimize infection, and allow for full-term or near full-term birth, such as from an early PROM event to between about 28 to about 34 weeks gestation.

Figure 1:
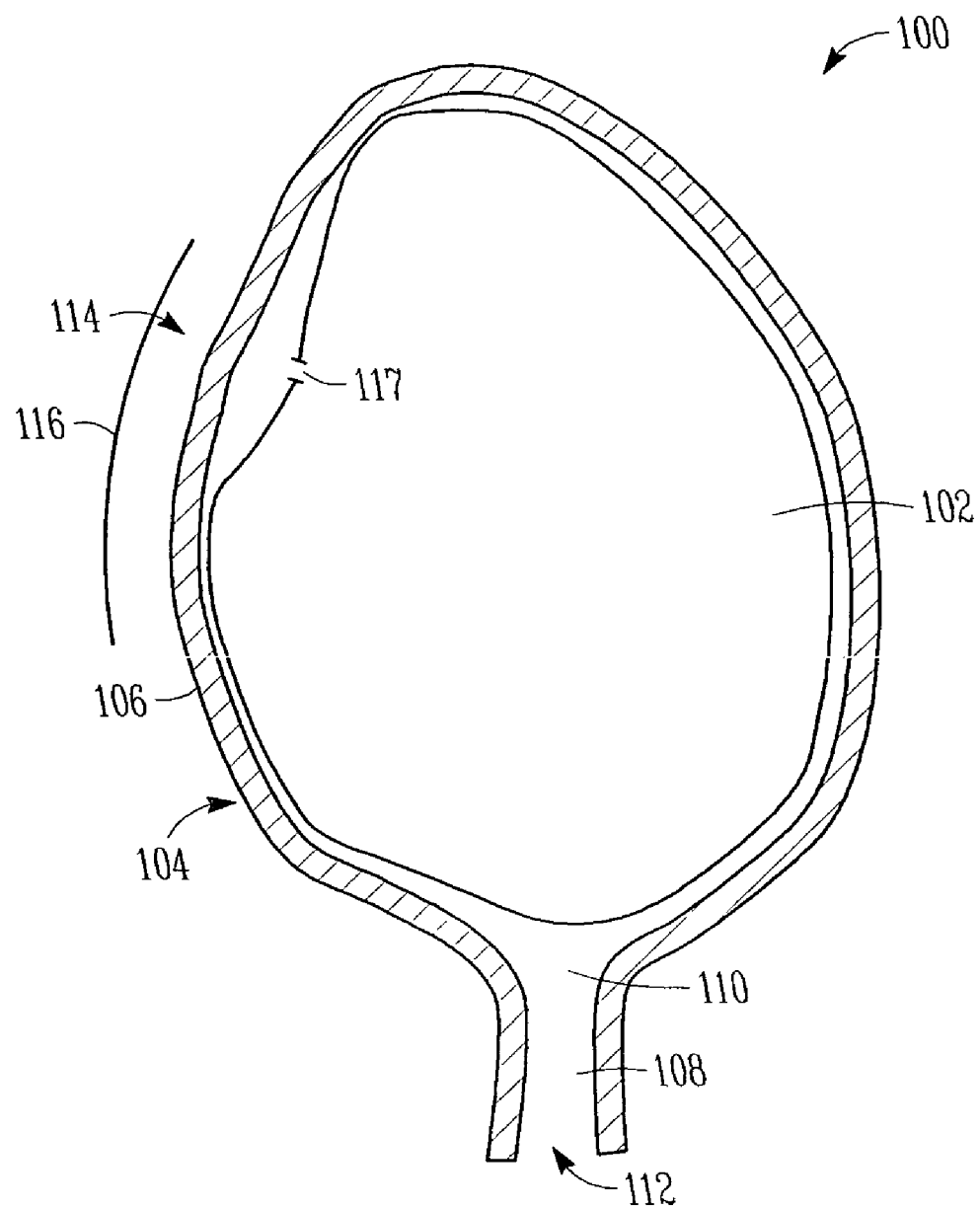
FIG. 1 illustrates an example schematic view of anatomical tissue structures including an amniotic membrane, a uterus, a cervix, and an abdominal wall, such tissue structures providing a suitable environment in which a cervical or uterine side wall occluder apparatus can be used.

As a matter of background, FIG. 1 illustrates some anatomical tissue structures 100 associated with pregnancy, including an amniotic membrane 102 for enclosing a fetus, a uterus 104, a uterine side wall 106, and a cervix (including a cervical canal 108 and an internal cervical os 110). The amniotic membrane 102 is not vascularized, slow to heal, uniquely configured, and is not easily accessible. Moreover, the location of an amniotic membrane rupture can be difficult to determine. For at least these reasons, the present apparatus, methods and kits, which are configured to inhibit or prevent leakage of amniotic fluid from the uterus 104 due to PROM, can provide great benefits not currently achievable in a safe and effective manner.

In some examples, a transvaginal access route 112 is used to implant a present apparatus including a support member and a fluid-resistant material. The transvaginal route 112 can traverse the vagina and the cervical canal 108 before entering the internal cervical os 110. Because a PROM patient has leakage of amniotic fluid due to an amniotic membrane 102 rupture, position of the patient so that the cervical canal 108 is raised above the uterus 104, i.e., the Trendelenburg position, can help create space in the uterus 104 near the internal cervical os 110 for insertion of the apparatus.

In some examples, a transabdominal access route 114 is used to implant a present apparatus including a support member and a fluid-resistant material. The transabdominal access route 114 extends though a portion of an abdominal wall 116 and provides a means to inhibit or prevent leakage of amniotic fluid from an amniotic membrane rupture 117, near a uterine side wall 106, directly in cases of surgical manipulations within the uterus 104.

Figure 2A:
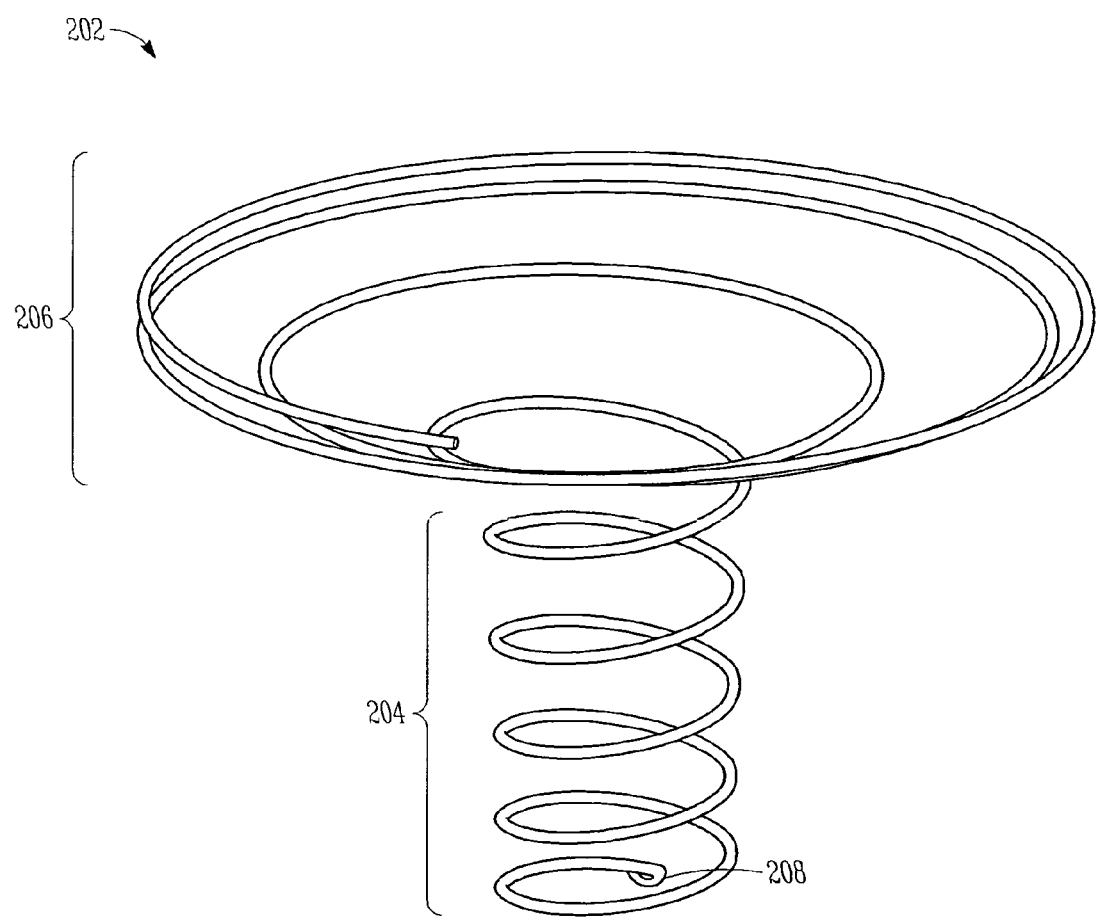
FIGS. 2A-2B illustrate an isometric view of example support members, configured for implant within a cervical canal, an internal cervical os, or a uterine side wall rupture location.
Figure 2B:
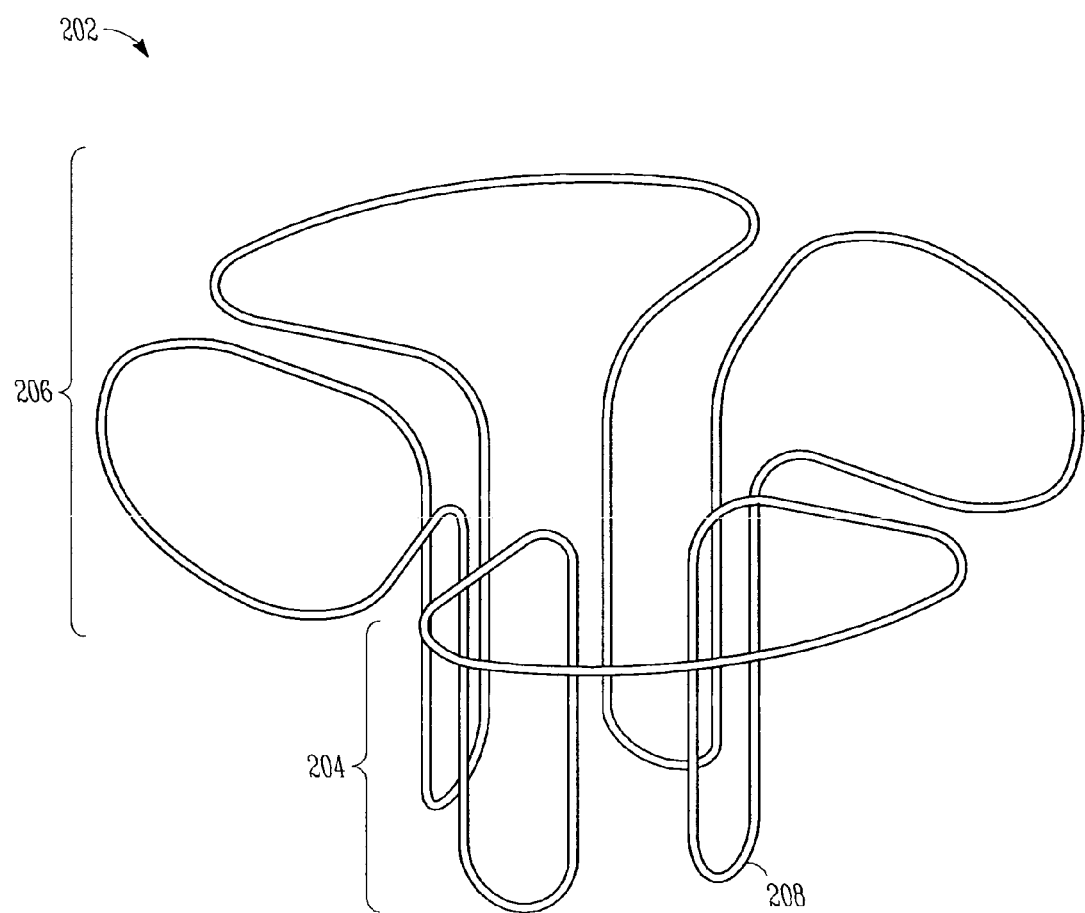

FIGS. 2A-2B illustrate isometric views of example support members 202. In some examples, the support member 202 can include a stent-like or other expandable structure that is transvaginally insertable 112 (FIG. 1) and can be deployed through, and fixated with, walls of the cervix. In an example, the support member 202 includes a stent-like structure, such as Boston Scientific's WALLSTENT™ ILIAC ENDOPROSTHESIS product.

Figure 3A:
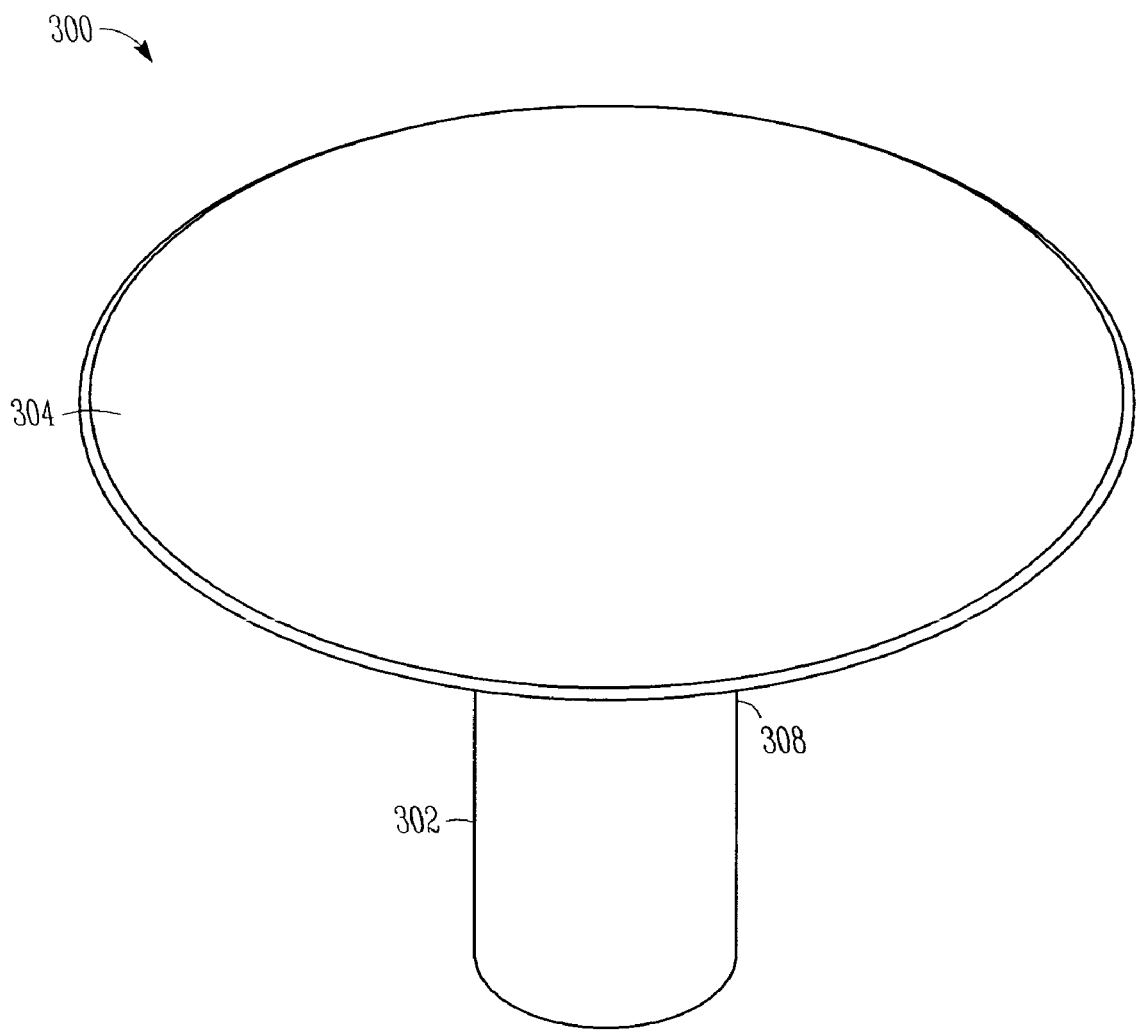
FIGS. 3A-3C illustrate an isometric view of example apparatus including a support member and a fluid-resistant material, configured for implant within a cervical canal, an internal cervical os, or a uterine side wall rupture location.
Figure 3B:
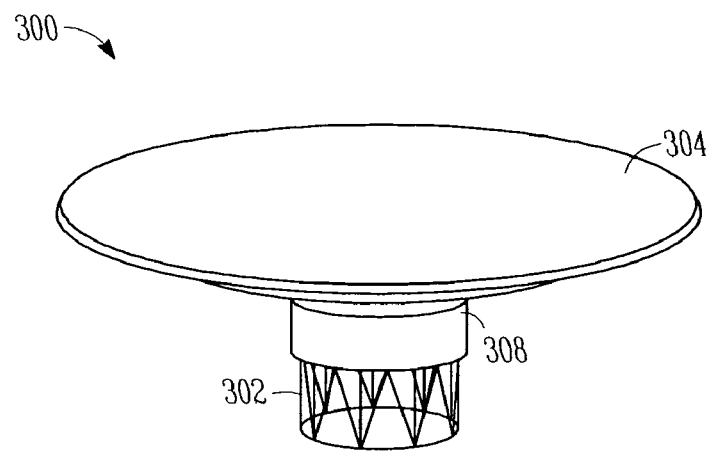
Figure 3C:
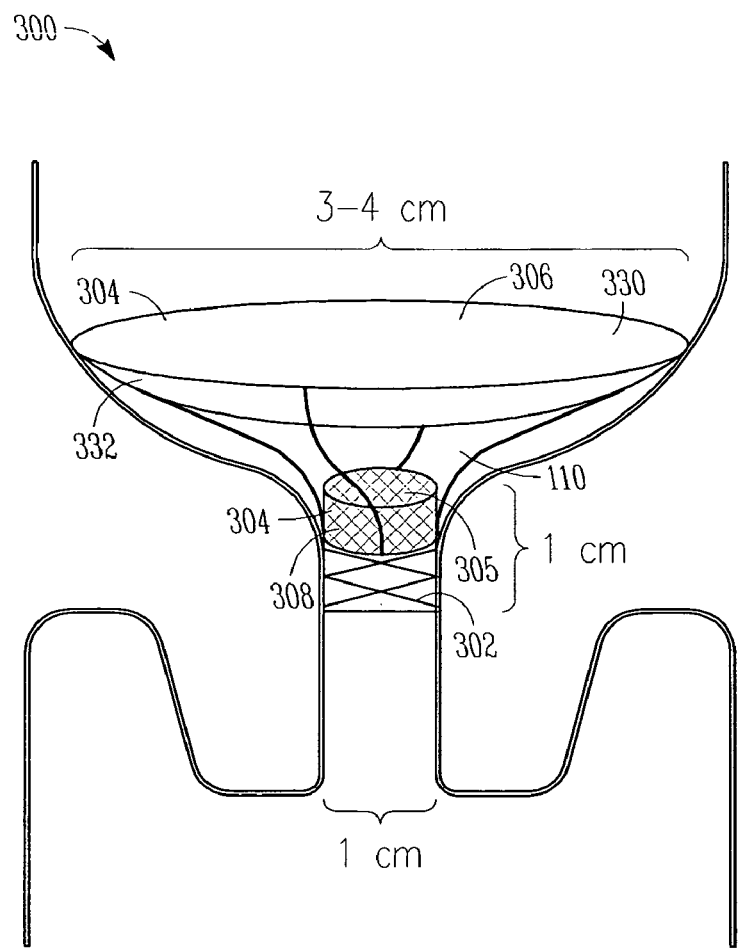

In some examples, as shown in FIGS. 2A-2B, the support member 202 can include a locating cylinder portion 204 and an integrated or attached diaphragm portion 206. The locating cylinder portion 204 can be configured to remain in the cervical canal 108 (FIG. 1) and serve anchoring purposes by expanding against wall portions of the cervical canal 108. The diaphragm portion 206 can be configured to support a fluid-resistant material, as shown in FIGS. 3A-3C, which contact wall portions of an amniotic membrane 102 (FIG. 1) or a uterus 104 (FIG. 1) to reduce or prevent loss of amniotic fluid. In some examples, the support member 202 does not include a locating cylinder portion 204. In some examples, the support member 202 does not include a diaphragm portion 206, but rather assumes a uniform diameter, expandable stent structure.

The support member 202 can include various dimensions, materials, and structure configurations. In some examples, the locating cylinder portion 204 can have a deployed, expanded diameter between about 0.25 centimeters (cm) to about 2.0 cm, and more preferably between about 1.0 cm to about 1.5 cm, and a pre-deployment (i.e., unexpanded) diameter between about 3 millimeters (mm) to about 8 mm. In some examples, the locating cylinder portion 204 can have a length of about 0.75 cm to about 2.5 cm. In some examples, the diaphragm portion 206 can have a deployed, expanded diameter of about 3 cm to about 4 cm, and a pre-deployment diameter between about 3 mm to about 8 mm. In some examples, as shown in FIG. 2A, the support member 202 can include a coil-like structure. In some examples, as shown in FIG. 2B, the support member 202 can include a mushroom-like structure. To aid in removal, the support member 202 can include a retrieval loop 208 at or near a bottom end portion (i.e., an outermost portion of the support member, which, when implanted, is nearest the exterior of a patient).

In various examples, the support member 202 or portions thereof can be configured to flex to fit local tissue variation at the time of implantation. Optionally, the support member 202 or portions thereof can be configured to conform to progressive changes in tissue over time, such as can be common during the gestational cycle. In some examples, the support member 202 includes Nitinol (a nickel titanium alloy) or other shape memory or expandable, conformable material. The support member 202 can include 0.010 inch diameter elastic Nitinol wire, which when exposed to body temperatures, assumes a pre-formed shape upon implantation. In some examples, the support member 202 resists cellular in-growth and adhesions, while in other examples, the support member 202 allows for or promotes selected cellular in-growth or adhesions.

FIGS. 3A-3C illustrate an isometric view of various biocompatible apparatus 300 including a support member 302 and a fluid-resistant material 304. In these examples, the apparatus 300 includes an expandable, biocompatible support member 302 and a fluid-resistant material 304 in the form of a fluid-resistant fabric or polymer. In some examples, one or both of the support member 302 or the fluid-resistant material 304 is coated or impregnated with bacterial control compounds to provide antibacterial release during use. In some examples, one or both of the support member 302 or the fluid-resistant material 304 is coated or impregnated with an antimicrobial agent, such as nano silver or chlorhexidine. The antimicrobial agents can provide broad antibiotic and yeast coverage to a patient. In some examples, the fluid-resistant material 304 can have a deployed, expanded diameter of about 3 cm to about 4 cm, and a pre-deployment diameter between about 3 mm to about 8 mm.

Figure 4:
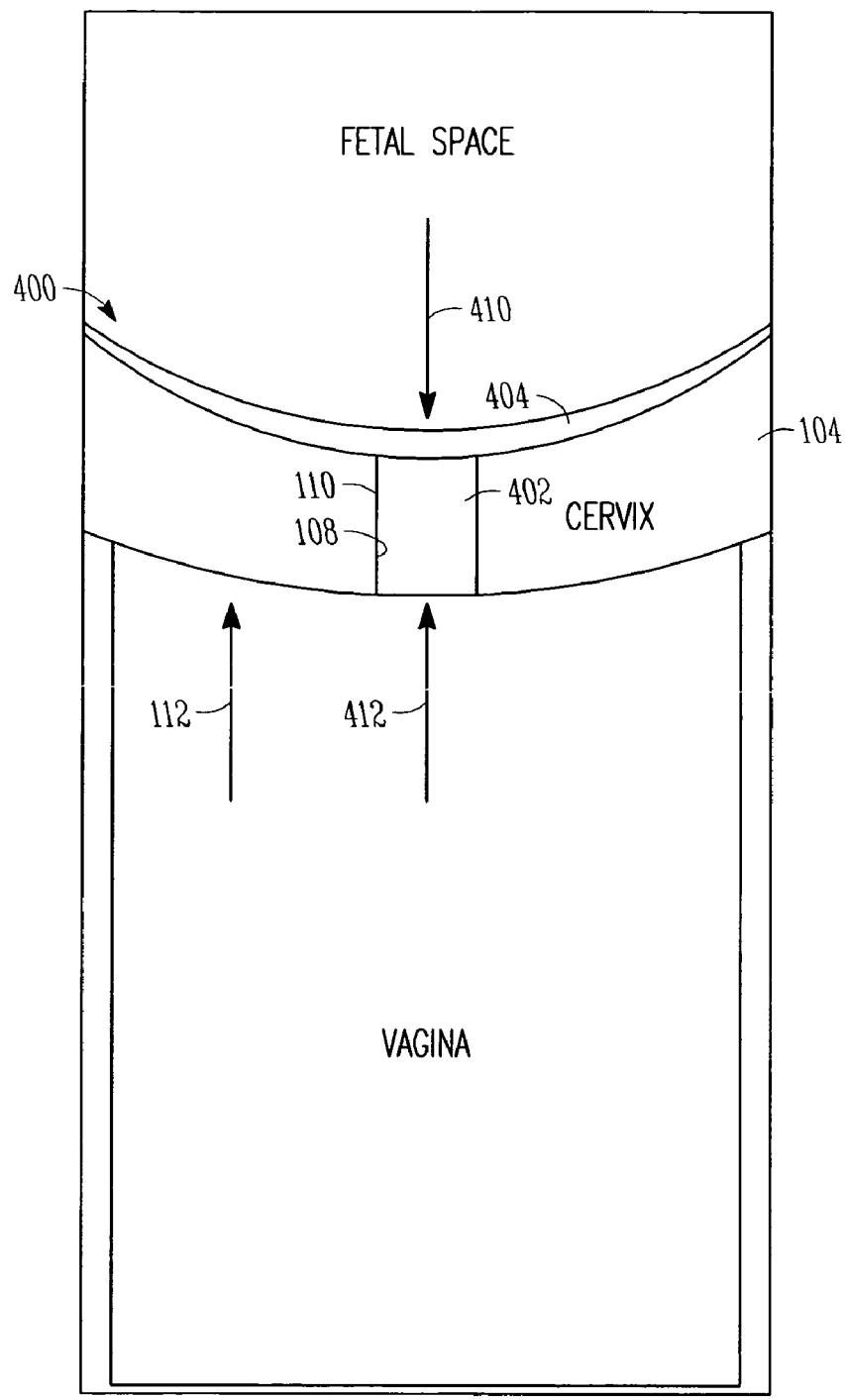
FIG. 4 illustrates a schematic view of an example apparatus including a support member and a fluid-resistant material retained within a cervical canal and internal cervical os.

FIGS. 3A and 3B illustrate that a top portion 308 of the support member 302 (i.e., an innermost portion of the support member, which, when implanted, is inserted nearest to an internal cervical os 110 (FIG. 1)) can open and position the fluid-resistant material 304 over the uterine side of the internal cervical os (see, e.g., FIG. 4). The fluid-resistant material 304 can then extend at least partially down a length of the support member 302 for sealing purposes. In the example of FIG. 3A, the fluid-resistant material 304 extends completely down the length of the support member 302; while in the example of FIG. 3B, the fluid-resistant material 304 extends only about 30-50% down the length of the support member 302. In some examples, it has proven helpful to not cover a bottom portion of the support member 302 to aid in apparatus removal via an exposed retrieval loop.

The fluid-resistant material 304 shown in FIGS. 3A and 3B includes PTFE or ePTFE, both of which are biocompatible and conformal materials. During manufacture, a PTFE or ePTFE tube of material can be heated and blow-molded using gas pressure. This blow-molded polymer tube can be coupled with the top portion 308 of the support member 302 using one or more crimps, one or more stitches, an adhesive, heat or other similar types of bonding, for example.

FIG. 3C illustrates that a top portion 308 of the support member 302 can be coupled to more than one fluid-resistant member 304. In some examples, the expandable support member 302 can be covered or coated on the top side portion 308 with a fluid-resistant material 305, such as GORE-TEX's® DUALMESH® PLUS Biomaterial product or other piece of fabric that is pliable, easy to work with, repels water, and optionally can be impregnated with anti-infection agents. Materials like GORE-TEX's® DUALMESH® PLUS include a plurality of small holes that can allow for tissue incorporation. Thus, over time, portions of the material can become integral with surrounding bodily tissue via tissue in-growth. In some examples, the fluid-resistant material 305 has a thickness about 0.25 cm to about 0.75 cm and is stitched to the support member 302 using a biocompatible thread. In addition, a second fluid-resistant material 306 can be coupled to the top portion 308 of the support member 302 in a manner similar to a parachute coupling to a pack. A first side 330 of the second fluid-resistant material 306 can be configured to promote cell adhesion. A second side 332 of the second fluid resistant material 306 can be coated with a water-activated adhesive to help bond the material 306 to underlying uterine tissues to promote sealing. It is believed that an apparatus 300 including more than one fluid-resistant member 304, as shown in FIG. 3C, can provide enhanced functionality (e.g., via redundant sealing) and may ease deployment during implantation via an atraumatic, extremely flexible top end portion.

As shown in FIG. 4, an apparatus 400 can be transvaginally inserted 112 and can be deployed through a cervical canal 108 and an internal cervical os 110 such that a fluid-resistant material 404 is centered over the area of the cervix and maintained in position with a support member 402 that projects through the cervical canal 108. An outer edge portion of the fluid-resistant material 404 can rest on an upper-facing surface of the uterus 104, as shown schematically in FIG. 4. It has been found that cervical changes often occur as the gestation period advances. These changes can include: a decrease in the cervical canal 108 length, a dilation of the cervical canal 108, a softening of the cervix, or a changing of the cervix from a posterior to an anterior position. Accordingly, one or both of the support member 402 and the fluid-resistant material 404 can be configured to conform to the cervical changes to help ensure proper sealing and diminish leaking of amniotic fluid from the uterus 104.

In some examples, the resistance of the fluid-resistant material 404 can be directional, such that it can be resistant to fluid penetration from a first direction 410 (e.g., from a uterus toward a vagina), but can permit fluid penetration from a second direction 412 (e.g., from within the support member 402 or administered from outside the body, through the vagina and support member 402, to the underside of the fluid-resistant material 404). In various examples, the fluid-resistant material 404 is fluid-impermeable in the first direction 410 at intrauterine pressures of about 20 millimeter of mercury (mmHg) to about 33 mmHg. This fluid-impermeability can allow amniotic fluid to refill the uterus 104 and fetal space without leaking through the cervical canal 108.

The fluid-resistance directionality of the fluid-resistant material 404 can be particularly useful to permit the apparatus 400 to be configured to allow diffusion or other delivery of a pharmaceutical drug composition (e.g., an antibiotic) or other substance through the covering material 404 while the support member 402 is implanted within the cervical canal 412 of a patient. Optionally, the fluid-resistant material 404 can be infused or coated with a pharmaceutical drug or other substance composition.

Figure 5:
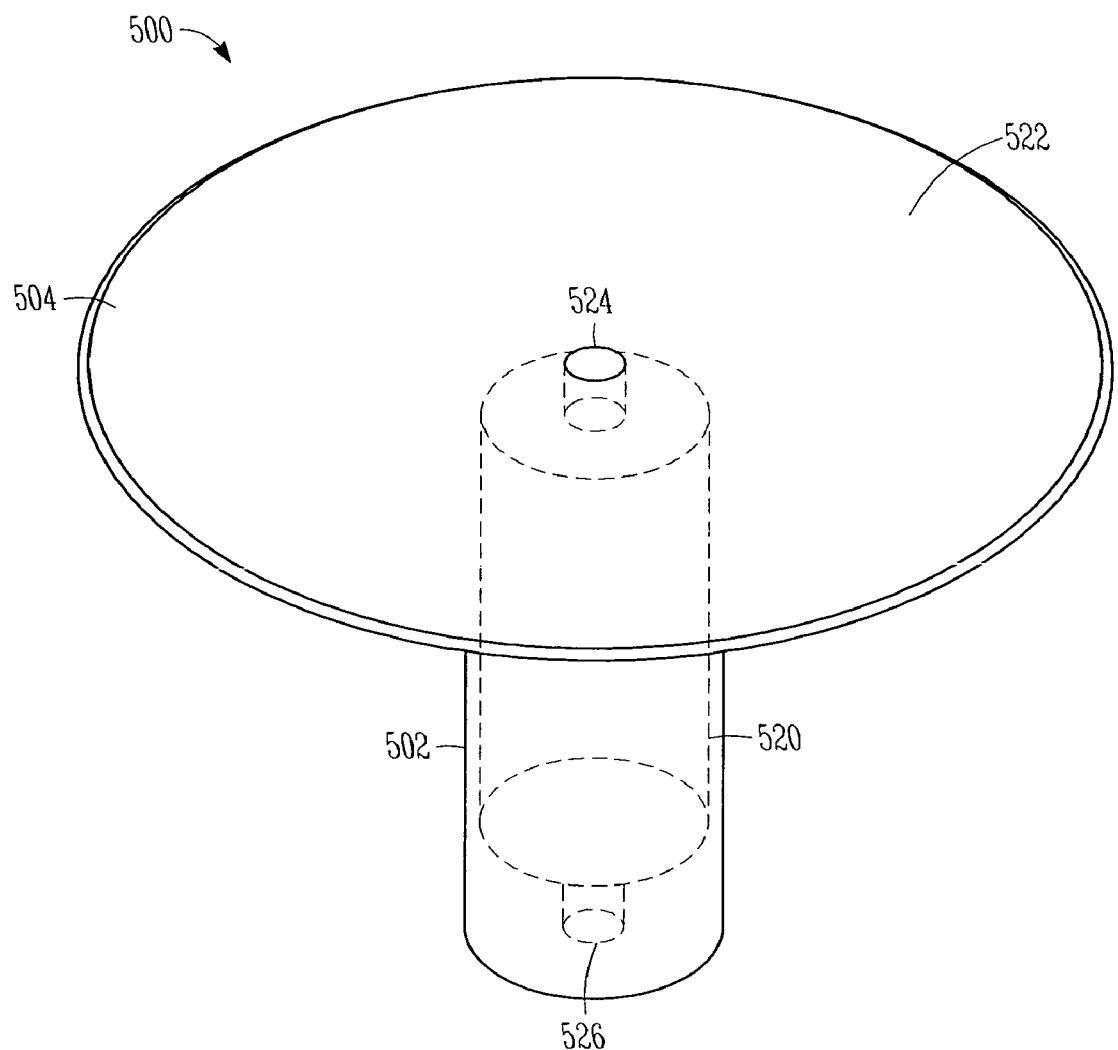
FIG. 5 illustrates an isometric view of an example apparatus including a support member, a fluid-resistant material, and a reservoir, the reservoir configured to store a pharmaceutical drug composition or other substance to be delivered to a patient.

FIG. 5 illustrates an example apparatus 500 including a reservoir 520. In some examples, the reservoir 520 is configured to store a pharmaceutical drug composition or other substance to be delivered to a patient. The reservoir can be carried at least partially within a support member 502, and can include means to allow drug or other substance delivery on a sustained release basis (e.g., days, weeks, or months) to the patient. In some examples, a top portion 522 of the apparatus (i.e., an innermost portion of the apparatus, which, when implanted, is inserted nearest to an amniotic membrane 102 (FIG. 1)) can include a pore 524 in fluid communication with the reservoir 520. The pore 524 can be constructed with a specific geometry appropriate to control the rate of release of the pharmaceutical drug composition or other substance to the uterus 104 (FIG. 1) or tissues within or near the uterus. Optionally, a micro-pump could be employed within the apparatus 500 to forcibly expel the drug composition or other substance from the reservoir 520 at a desired rate.

In some examples, the reservoir 520 can include a distally-located port or other opening 526 allowing the reservoir 520 to be filled or re-filled after the apparatus 500 is deployed within a cervical canal 108 (FIG. 1) and internal cervical os 110 (FIG. 1). In this way, the apparatus 500 can optionally remain small enough to easily pass through a transvaginal access route 112 (FIG. 1), for example, to a desired membrane rupture location. Depending on the required drug or other substance concentration, the pharmaceutical composition can be in the form of a solid, a concentrated aqueous or other solution, a resin suspension, or combination thereof.

The reservoir 520 can be molded or otherwise formed from a flexible material that is impermeable to the drug or other substance which will fill the reservoir 520. The reservoir 520 can be formed by a channel through an interior of the support member 502. Optionally, a wick extension from the reservoir 520 can be provided to aid in medication release to the uterus 104 or tissues within or near the uterus. The wick extension can be secured within the reservoir 520 in fluid communication with the drug or other substance stored therein, and can extend through the pore 524, for example. The wick extension can be formed of a material suitable to transmit medication from the reservoir 520 to the patient, such as an absorbent, cloth-like material. The use of a wick extension can help assure constant contact between the drug or other substance stored within the reservoir 520 and desired tissues of the patient.

Figure 6:
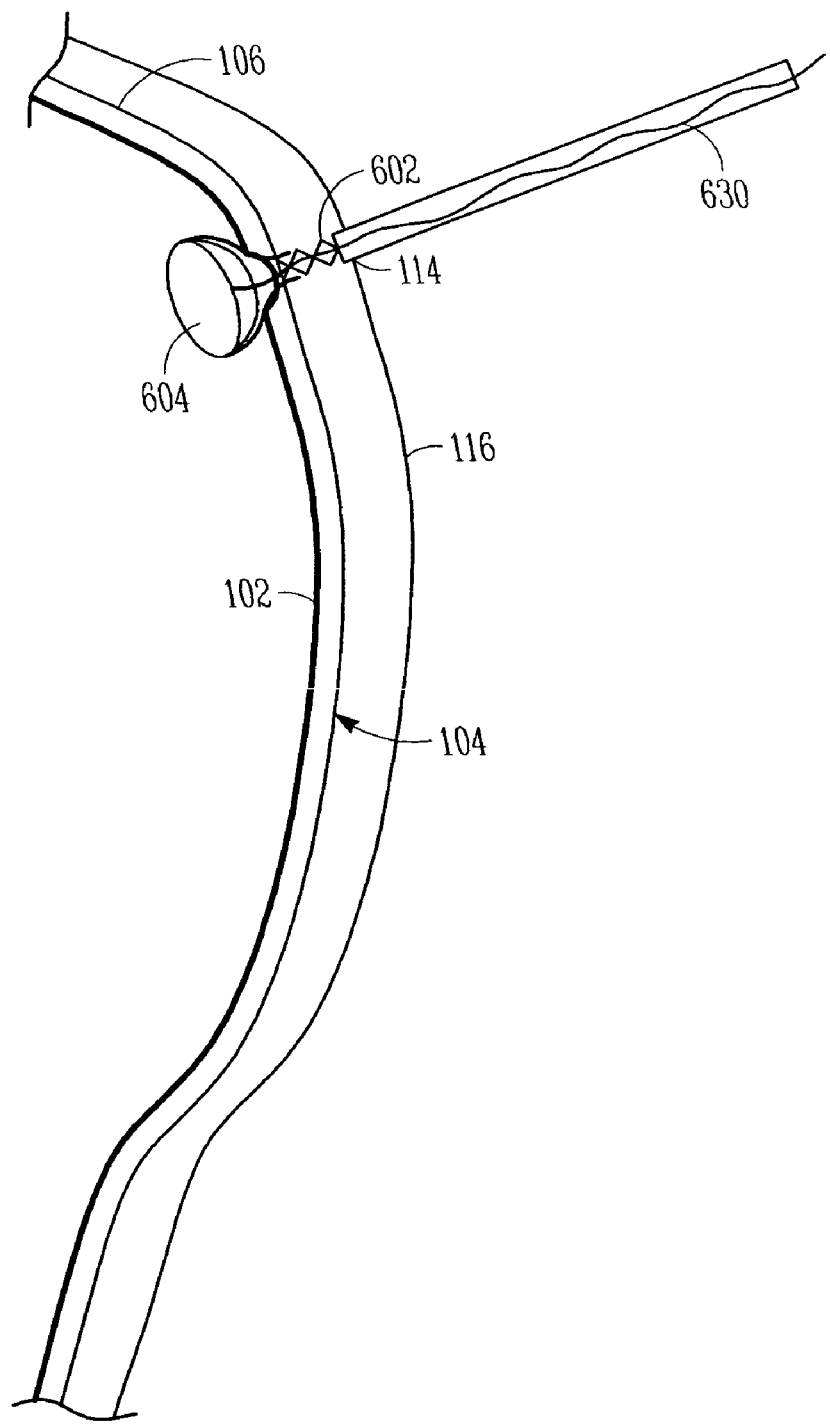
FIG. 6 illustrates a schematic view of an example apparatus including a support member and a fluid-resistant material retained within a uterine side wall rupture location.

FIG. 6 illustrates a schematic view of an example apparatus 600 including a support member 602 and a fluid-resistant material 604 retained within a uterine side wall 106 adjacent an abdomen wall 116. It has been found that beyond PROM occurring at or near the internal cervical os 110 (FIG. 1), a second type of PROM can occur. This second type of PROM is known as iatrogenic PROM and occurs most commonly as a complication of fetoscopy. With iatrogenic PROM, an amniotic membrane 102 rupture occurs somewhere on the side of the uterus 104 with amniotic fluid tracking between the membrane 102 and the uterine side wall 106 for a distance until it gets to the internal cervical os 110.

To this end, the present inventors have conceived an apparatus 600, which is smaller than the apparatus disclosed above and configured for cervical placement. This smaller apparatus 600 can be implanted via a transabdominal access route 114 for the prevention of iatrogenic PROM. In some examples, a location cylinder portion of the support member 602 can have a deployed, expanded diameter between about 0.25 cm to about 0.5 cm and a length of about 0.25 cm to about 0.5 cm. In some examples, the fluid-resistant material 604 can have a deployed, expanded diameter of about 0.75 cm to about 1.25 cm, such as about 1.0 cm. A detachable string 630 can be used to pull the fluid-resistant material 604 back up against the rupture in the amniotic membrane 102 during implantation.

The transabdominal apparatus 600, like the larger cervical apparatus, can be implanted using a catheter. While it is not always possible to determine the location of an iatrogenic rupture accurately, when the location can be determined, direct sealing of the rupture using the apparatus 600 can be beneficial. Optionally, a larger apparatus configured for cervical placement can be used in conjunction with apparatus 600 to further prevent amniotic fluid from leaking out of the uterus 104 and through a cervical canal 108 (FIG. 1).

A retail kit may also be packaged for consumer purchase. The kit may include an apparatus comprising a support member and a fluid-resistant material covering or otherwise coupled to a portion of the support member. The kit may also include a set of instructions for using the apparatus. In some examples, the kit includes a pharmaceutical drug composition or other substance incorporated with the fluid-resistant material or stored in a reservoir carried by the support member, thereby allowing a treating physician to customize an amount and delivery means of drug or other substance applied to a patient. In some examples, the kit includes one or more insertion or removal tools for implanting and withdrawing the apparatus.

Figure 7:
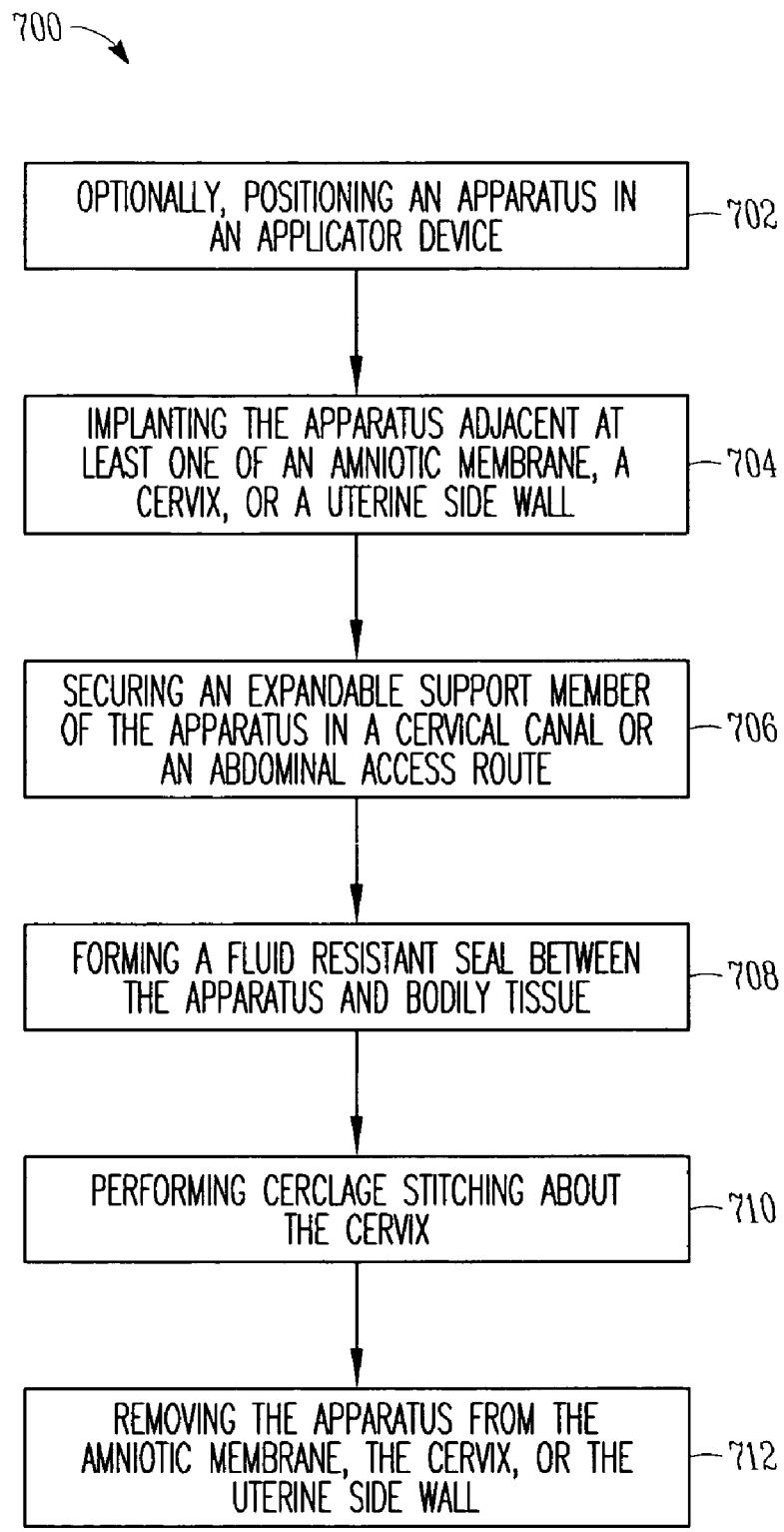
FIG. 7 illustrates an example method of using an apparatus including a support member and a fluid-resistant material to temporarily occlude or partially occlude a cervical canal, an internal cervical os, or a uterine side wall rupture location after PROM.

FIG. 7 illustrates an example method of using an apparatus including a support member and a fluid-resistant material to temporarily occlude or partially occlude a cervical canal, a cervical os, or a uterine side wall rupture location after PROM.

At 702, an apparatus, including an expandable support member and a fluid-resistant material, is optionally positioned in an applicator device, such as a delivery catheter, having an adjustable mechanical stop to ensure proper implant depth. In various examples, the apparatus can be configured to be implanted with a single hand of a treating physician through a vagina to the cervical canal. Implantation can be facilitated by the applicator device. In some examples, the applicator device can have an inner diameter between about 0.25 cm to about 1 cm and a length of about 35 cm. In other examples, the length of the applicator device can be less than 35 cm. When loaded into the applicator device, the expandable support member (e.g., Nitinol wire coil) can be pulled into a cannula of the device, pulling the coil shape (see, e.g., FIG. 2A) into a relatively straight shape. The fluid-resistant material coupled to a top portion of the support member (see, e.g., FIG. 3A) can also be at least partially pulled into the cannula.

At 704, the apparatus is implanted adjacent at least one of an amniotic membrane, a cervix, or a uterine side wall. To deploy the apparatus from the applicator device, the applicator device is advanced through the cervix or abdomen (either visually or under guidance). When the expandable support member starts to emerge from the cannula, it is no longer constrained and beings to recover its coiled or otherwise expanded shape. As the support member "remembers" its shape, it can pull and expand the fluid-resistant material into position and form a cupped, domed or disc-shaped cap. The bottom portions of the support member can expand in the cervical canal or an abdominal access route, at 706.

At 708, the fluid-resistant material can extend partially into the cervix or an amniotic membrane to help ensure a seal with bodily tissue. Proper placement/implantation of the apparatus can be verified by physician visualization or sonography.

At 710, the method can further include performing cerclage stitching about the cervix, to temporarily seal or occlude the cervical canal and assure the apparatus is not expelled from the cervical canal until delivery of the fetus is to occur or until desired. In some examples, the method of 710 is only used to treat spontaneous PROM and not iatrogenic PROM.

At 712, the apparatus can be removed. In some examples, removal of the apparatus is performed using a special remover device. In some examples, removal of the apparatus is performed using existing hospital tools or equipment. The remover device can be configured to hook a retrieval loop at an outermost, bottom end of an implanted apparatus, force can then be applied, and the apparatus can be removed.

Figure 8A:
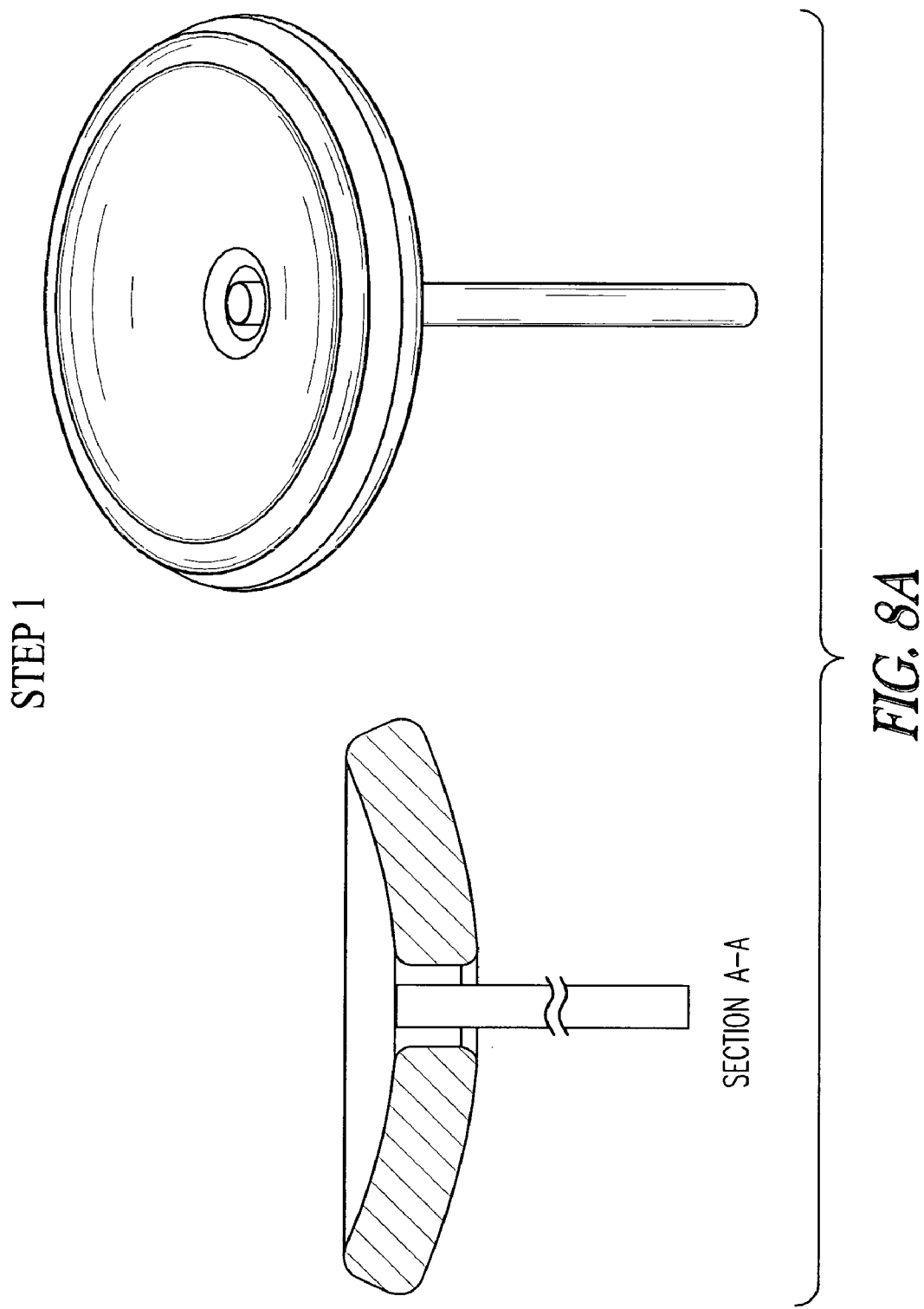
Figure 8B:
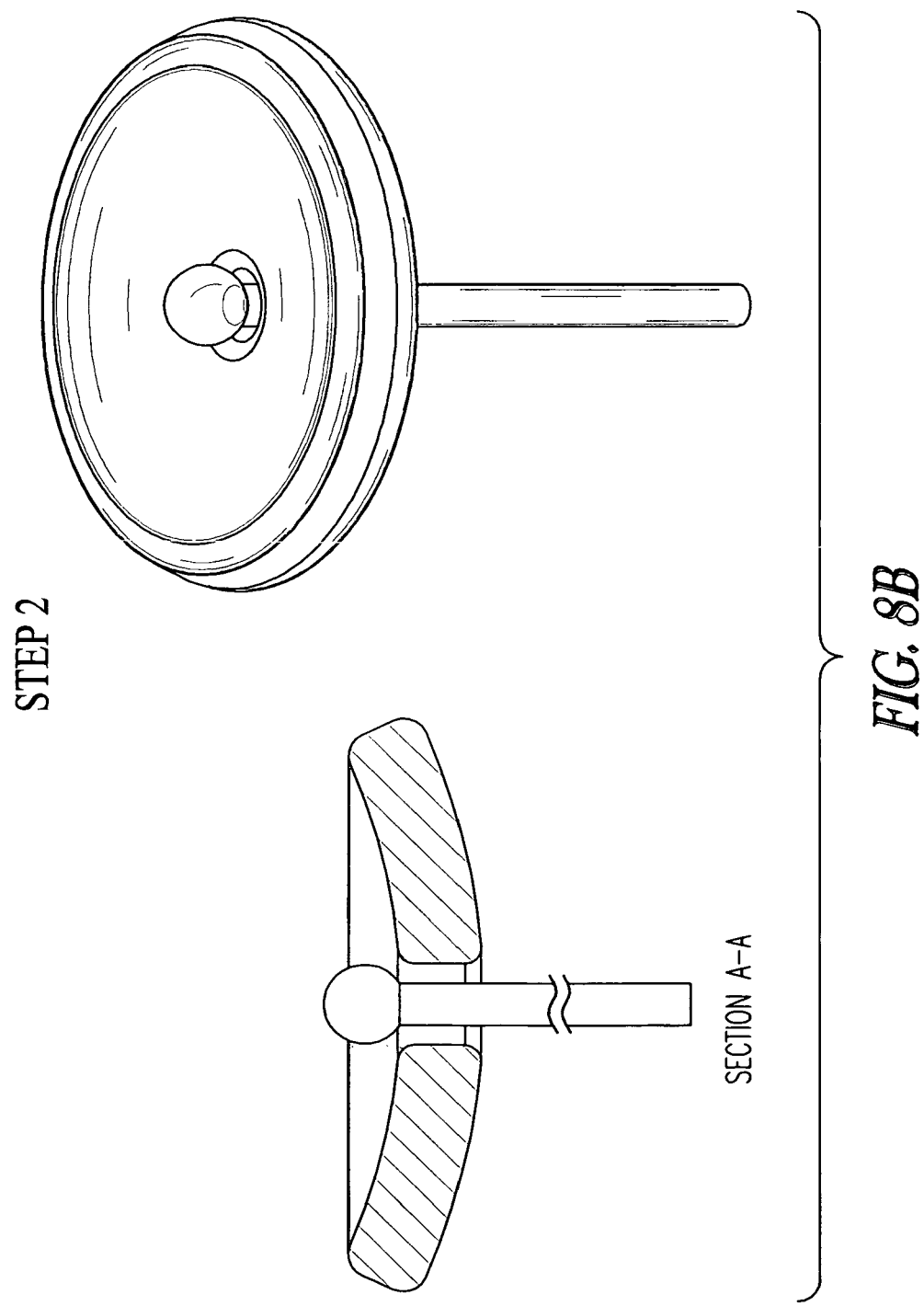
Figure 8E:
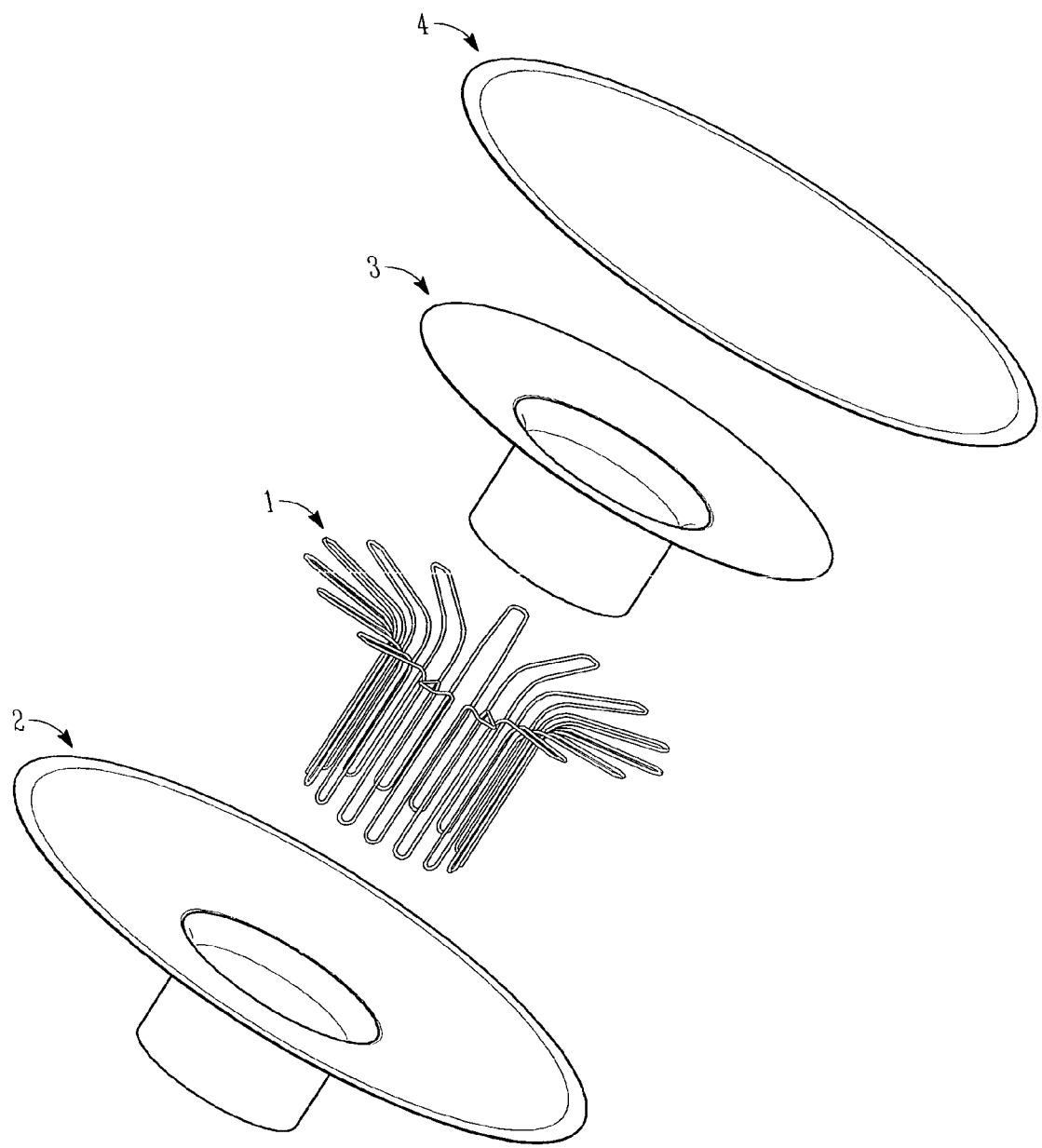

FIGS. 8A-8E illustrate an example of an apparatus and method of use such as for cervical occlusion. In the example of FIG. 8A (step 1), after PROM, an occlusion device delivery cannula can be inserted through the cervix just proximal of the cervical os on the uterine side. In the example of FIG. 8B (step 2), the occlusion device can be inflated, such as with isotonic saline (or similar medical fluid), such as for providing a cushion against the fetal head, and forming a deployment void in the uterine cavity. In the example of FIG. 8C (step 3), the occlusion device can be fully inflated, and released from the delivery cannula. In an example, the proximal end of the device can include exposed Nitinol (NiTi) struts in a serpentine (or "daisy) configuration, which can expand due to body temperature, and can purchase the cervical canal wall. The exposed struts can also enable reformation of the mucus plug, such as for providing a secondary barrier to ascending infection. In the example of FIG. 8D (step 4), the isotonic fluid drains from the occlusion device, forming a membrane barrier at the uterine side cervical os, such as for forming a plug positioned and partially sealed by the NiTi wire "daisy" and allowing the membrane to form a flap-type seal. The example of FIG. 8E shows an example of an exploded view of the device, with these components:

1) Skeletal wire frame (e.g., "daisy")—can include a NiTi or other shape memory material, in an example.
2) Base membrane—can include thermoplastic polyurethane, PTFE, or similar material, in an example.
3) Retention membrane—can bond skeletal wire frame to base membrane; can include a thermoplastic polyurethane, PTFE, or similar material, in an example.
4) Top membrane—can form "balloon" section; can include thermoplastic polyurethane, PTFE, or similar material.

In an example, construction can include RF welding or other bonding of items 2 & 3, encapsulating item 1 therebetween, and then RF welding or bonding item 4 on top.

Closing Notes:

Apparatus, methods and kits which, when installed or used, occlude or partially occlude a cervical canal, the internal opening of a cervical canal (cervical os), or a uterine side wall rupture location, such as to inhibit or prevent bacterial access and leakage of amniotic fluid resulting from PROM. The present apparatus can include an expandable support member of a biocompatible and non-toxic material. In some examples, the support member can include a top portion having a first diameter and a bottom portion having a second diameter, which is less than the first diameter. In some examples, the support member can include an expandable stent of a suitable length and substantially uniform diameter to be inserted in a non-dilated cervical canal or a transabdominal access route. In various examples, the apparatus further includes a fluid-resistant fabric, polymer, substance or other material placed over or otherwise coupled to at least the top portion of the support member.

To date, no known effective blocking or therapy devices are available to treat the effects of PROM. Advantageously, the present apparatus, methods and kits are believed to provide a safe and effective means to inhibit or prevent continuing loss of amniotic fluid from the uterus (thereby restoring membrane function) after PROM has occurred. In this way, pregnancy can be prolonged to advance fetal development and adverse events to the fetus resulting from decreased amniotic fluid can be diminished. Additionally, the present apparatus, methods and kits can provide a patient the benefit of a continuous pharmacologic effect via drug or other substance release from a reservoir.

The above Detailed Description includes references to the accompanying drawings, which form a part of the Detailed Description. The drawings show, by way of illustration, specific embodiments in which the present apparatus, methods and kits can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable Inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, "the membranes of pregnancy" or similar is used to refer to the particular anatomy of the human membrane system that is formed to enclose a fetus.

In the appended claims, the terms "including" and "in which" are used as the plain-English equivalents of the respective terms "comprising" and "wherein." Also, in the following claims, the terms "including" and "comprising" are open-ended, that is, a system, assembly, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. For instance, the apparatus, methods and kits disclosed herein can provide techniques for treatment of other lesions, natural or surgical, beyond PROM, which allow leakage of a fluid. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. An implantable occlusion apparatus, comprising:
  an expandable support member extending from a first end portion to a second end portion, the expandable support member sized to pass through a cervical canal or a transabdominal access route and be positioned within at least one of an amniotic membrane, a cervical os, or a uterine side wall; and
  a first and a second fluid-resistant material, the first fluid-resistant material covering, or coated on, a first end portion of the expandable support member and the second fluid-resistant material extending beyond and coupled to, the first end portion of the expandable support member by crimps thread, adhesive or heat bonding,
  wherein one or both of the first and second fluid-resistant materials are configured to occlude or partially occlude the cervical os or a rupture of the amniotic membrane near the uterine side wall.

2. The apparatus of claim 1, wherein the expandable support member includes a stent-like structure having a uniform diameter from the first end portion to the second end portion.

3. The apparatus of claim 1, wherein a bottom surface of the second fluid-resistant material is coated with a adhesive.

4. The apparatus of claim 1, wherein the first end portion is configured to support one or both of the first and second fluid-resistant materials and the second end portion is configured to anchor against a wall of the cervical canal or the transabdominal access route.

5. The apparatus of claim 1, wherein the first fluid-resistant material extends at least partially down a length of the expandable support member.

6. The apparatus of claim 1, wherein the second end portion of the expandable support member includes an expanded diameter between about 0.25 cm to about 2.0 cm and a pre-expanded diameter between about 3 mm to about 8 mm.

7. The apparatus of claim 1, wherein one or both of the first and second fluid-resistant materials include an average implanted diameter between about 0.75 cm to about 1.25 cm or between about 3 cm to about 4 cm.

8. The apparatus of claim 1, wherein the expandable support structure includes a shape-memory alloy.

9. The apparatus of claim 1, wherein one or both of the first and second fluid-resistant materials include polytetrafluoroethylene, expanded polytetrafluoroethylene, a tightly woven fluid-resistant, nano-fiber material, silicone, polyurethane, a tissue, or a natural material.

10. The apparatus of claim 1, wherein a seal between one or both of the first and second fluid-resistant materials and adjacent bodily tissue includes sufficient adherence to withstand a pressure of about 20 mmHg or more without substantial fluid leakage through the cervical os.

11. The apparatus of claim 1, wherein one or both of the first and second fluid-resistant materials are resistant to fluid penetration in a first direction and permit fluid penetration in a second direction, opposite the first direction.

12. The apparatus of claim 1, wherein one or both of the first and second fluid-resistant materials include at least one pharmaceutical substance.

13. The apparatus of claim 1, comprising a reservoir contained at least partially within the expandable support member, the reservoir configured to carry a pharmaceutical substance.

14. A kit comprising:
  the apparatus according to claim 1; and
  a set of instructions for using the apparatus to occlude or partially occlude at least one of an amniotic membrane, a cervical os, or a uterine side wall.

15. The kit of claim 14, comprising an applicator device having an adjustable mechanical stop to ensure proper implant depth, the applicator device configured to access at least one of the amniotic membrane, the cervical os, or the uterine side wall.

16. A method comprising:
  implanting an apparatus including an expandable support member, a first fluid-resistant material, and a second fluid-resistant material adjacent at least one of an amniotic membrane, a cervical os, or a uterine side wall, the first fluid-resistant material coupled to at least a first end portion of the expandable support member and the second fluid-resistant material extending beyond and coupled to, the first end portion of the expandable support member by crimps, thread, adhesive or heat bonding;
  securing the expandable support member in a cervical canal or an abdominal access route, including expanding one or more portions of the expandable support member to bias against a wall of the cervical canal or the abdominal access route; and
  providing a replacement membrane at or near an amniotic membrane rupture location, including forming a seal with one or both of the first and second fluid-resistant materials and the amniotic membrane or a uterine side of the cervical os, to retain amniotic fluid.

17. The method of claim 16, comprising performing cerclage stitching about the cervix after inserting the apparatus.

18. The method of claim 16, comprising releasing a pharmaceutical substance stored in a reservoir at least partially positioned within the expandable support member.

19. The method of claim 18, comprising refilling the reservoir with a pharmaceutical substance.

* * * * *